United States Patent [19]
Miller et al.

[11] 4,172,105
[45] Oct. 23, 1979

[54] PEDIATRIC CARTRIDGE HUMIDIFIER

[75] Inventors: Kenneth G. Miller, Palatine; Martin Foley, Wheeling, both of Ill.

[73] Assignee: Respiratory Care, Inc., Arlington Heights, Ill.

[21] Appl. No.: 12,391

[22] Filed: Feb. 15, 1979

[51] Int. Cl.$^2$ .................. A61M 15/00; B01F 3/04
[52] U.S. Cl. .................... 261/66; 128/186; 128/192; 261/72 R; 261/104; 261/154; 261/DIG. 65
[58] Field of Search ............... 261/66, 72 R, 104, 107, 261/142, 78 A, 121 R, 152–156, DIG. 65; 128/186, 188, 192–194, 212, 185; 219/271–275, 535

[56] References Cited
U.S. PATENT DOCUMENTS

| | | |
|---|---|---|
| 3,771,721 | 11/1973 | Van Amerongen ......... 261/DIG. 65 |
| 3,807,713 | 4/1974 | Cornett et al. ............. 261/DIG. 65 |
| 3,851,645 | 12/1974 | Connel .......................... 128/188 |
| 3,874,379 | 4/1975 | Enfield et al. ............... 261/DIG. 65 |
| 4,010,748 | 3/1977 | Dobritz ........................ 261/DIG. 65 |
| 4,110,419 | 8/1978 | Miller ............................. 261/142 |

FOREIGN PATENT DOCUMENTS 1347054 11/1963 France ............................. 261/DIG. 65

*Primary Examiner*—Richard L. Chiesa
*Attorney, Agent, or Firm*—Eric P. Schellin; Joseph P. Nigon

[57] ABSTRACT

A previously disclosed cartridge type humidifier apparatus including a separate heater module with a cylindrical opening for replaceably receiving therein disposable cylindrical humidifier cartridge modules, having a housing containing a replenishable water supply, is employed as a water supply source for producing an aerosol with an oxygen supply for pediatric inhalation therapy. The cartridge modules each have a tubular metal main body adapted for a sliding fit within a complimentary tubular walled heater. The metal tubular body has rigid plastic top and bottom end portions. The plastic top end portion is a cap with a center axial gas inlet tube, and a separate transverse gas delivery pipe, the cap forming a closed air space over a pool of humidifying liquid. Each cartridge includes an absorption column, preferably of the cylindrical tube form which is adapted to lay closely adjacent and draw water up along the cartridges cylindrical metal body which serves as the evaporating surface when heated by the heater modules. The gas to be humidified is dispersed within a hollow chamber formed between the gas inlet pipe projecting concentrically into the cartridge, and the radially spaced wall of the main cartridge body and absorption column. The inlet tube terminates above the water. The water is introduced into the lower end portion of the apparatus.

5 Claims, 3 Drawing Figures

PEDIATRIC CARTRIDGE HUMIDIFIER

BACKGROUND OF THE INVENTION

The present invention relates to a modification of an inhalation therapy device for use as a pediatric ventilator.

U.S. Pat. No. 3,771,721 issued Nov. 13, 1973, relates to inhalation therapy in the medical art of treating with oxygen or a mixture of oxygen and air having a high moisture content. Several classes of devices including atomizers and humidifiers are adapted for such treatments. With respect to atomizers or nebulizers as they are often called, a heretofore known system for inhalation therapy comprises a container for pure water which has means enabling operation of the container in one of several modes.

U.S. Pat. No. 4,110,419 issued Aug. 29, 1978, relates to a cartridge type humidifier apparatus that includes a separate heater module with a cylindrical opening for replaceably receiving therein disposable cylindrical humidifier cartridge modules. The cartridge modules each have a tubular metal main body adapted for a sliding fit within a complimentary tubular walled heater. The metal tubular body has rigid plastic top and bottom end portions with a separate transverse gas delivery pipe, the cap forming a closed air space over a pool of humidifying liquid. The gas to be humidified is dispersed within a hollow chamber formed between the gas inlet pipe projecting concentrically into the cartridge and the radially spaced wall of the main cartridge body and absorption column. The inlet tube terminates above the water. The subject matter of this patent is incorporated herein by reference. The instant device is a modification of the structure disclosed in this patent to provide a pediatric cartridge humidifier.

SUMMARY OF THE INVENTION

The present invention is hereby concerned with a modification of the device covered in U.S. Pat. No. 4,110,419 that provides breathable inhaled gases that are moisture laden with large quantities of water, for pediatric use. This modification is accomplished by positioning a first tubular T in the conduit connecting the reservoir with the cylindrical cartridge. This first T conduit has a check valve therein that allows flow from the reservoir to the cartridge but not the reverse. This first T is connected by means of a conduit to a second T positioned above the reservoir. One arm of the second T is connected to the upper end portion cap means. The other arm, the second T, contains a restrictor and is connected to the reservoir of aseptic liquid.

By use of this modification water is transferred from the reservoir to the cartridge only when the pressure in the cartridge is less than the sum of differential water level head plus reservoir pressure. In addition, the restrictor maintains the pressure in the reservoir constant so that the reservoir does not expand and contract and is a compliant factor in the system. By use of this modification water is transferred from the reservoir to the cartridge only when the level in the cartridge is below that of the reservoir. A sight tube is mounted on the cartridge heater to allow the monitoring of the water level in the cartridge since the level of the water in the reservoir may differ from the level in the cartridge. This also allows monitoring of cartridge dead space and a label, calibrated in ml of dead space, is placed on the heater.

The other elements of the device are identical with the structure disclosed in U.S. Pat. No. 4,110,419.

DETAILED DESCRIPTION OF THE PREFERRED EMBODIMENT

Since the instant application covers the modification of the high volume disposable and semi-disposable cartridge humidifier with-self contained cartridge sterilizing means disclosed and claimed in U.S. Pat. No. 4,110,419. Only the essential portions of this modified apparatus will be discussed in detail.

Figure 1:
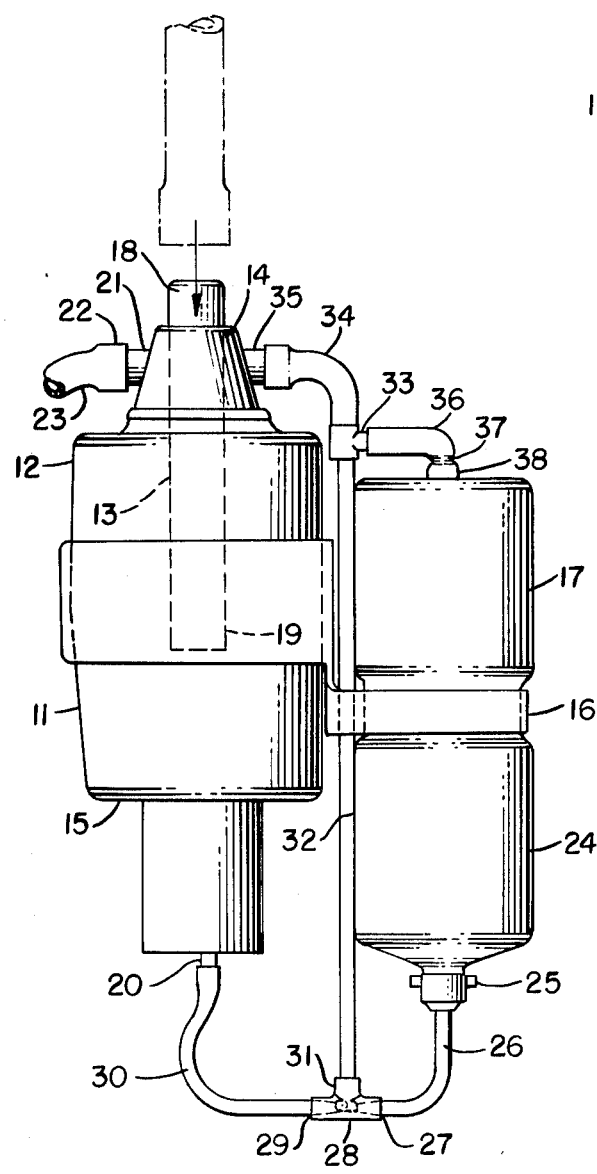
FIG. 1 is a perspective view of the assembled humidifying apparatus according to one form of the invention.
Figure 2:
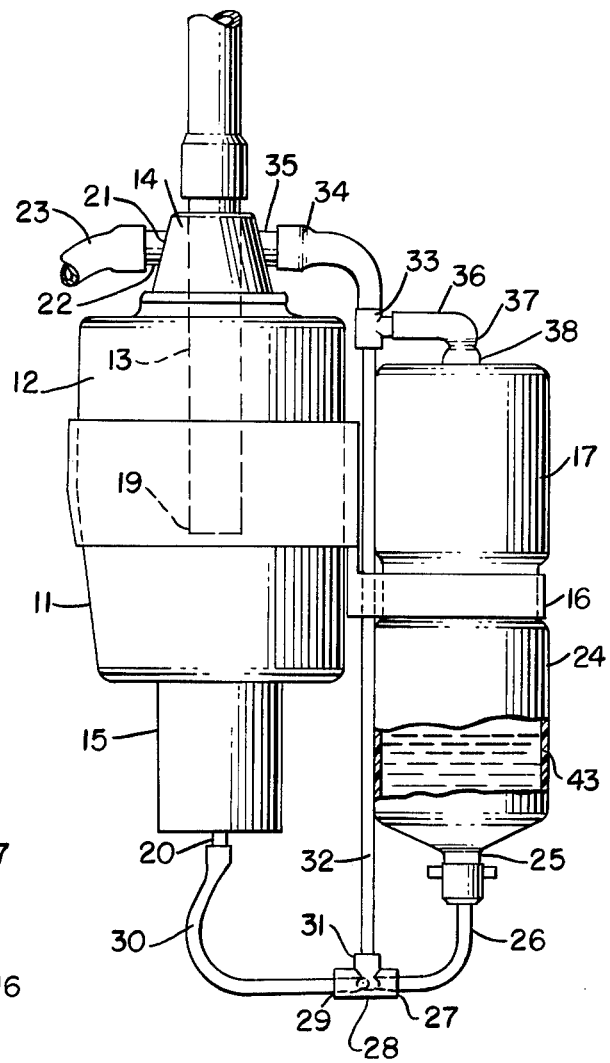
FIG. 2 is another perspective view of the invention with a portion of the structure shown in cross section.

Reference is made to FIGS. 1 and 2 wherein the modification of the humidifier and nebulizer assembly is generally indicated by reference numeral 11. The assembly comprises a combined heater cartridge supporting means 12 with a disposable or semi-disposable type humidifier cartridge module 13 shown in dotted lines which is provided with a preferably non-metallic top body and end cap 14 and a similar non-metallic bottom end cap or liquid contacting portion 15. The details of the heater and cartridge supporting module are described in detail in the above-identified application and will not be repeated here.

Additionally, the supporting means 12 is provided with a bracket means 16 to support therewith a suitably prepared water supply thermoplastic bottle reservoir 17 in predetermined ratio, a relationship to be further explained hereinafter. One type of such water supply 17 with which a system hereof is designed to work as aseptically prefilled bottle known as Concha ®, preferably the Concha ® 1500 (1500 ml) marketed by Respiratory Care, Inc., of Arlington Heights, Illinois. The cartridge is contained in a housing shell 12 and is provided with a preferably non-metallic topping cap 14 and a similar non-metallic bottom end cap 15. Cap 14 is provided with an axially centered gas inlet tube 18 shown in dotted line in the FIGS. 1 and 2. Since the details of this modification are not concerned with the internal structure of the apparatus this structure will not be described in detail in this application. Suffice to say that the tube 13 is of a length so that the inner edge 19 projects a substantial distance down into the cartridge body sleeve but terminates above the level of the water which is introduced into the bottom portion of the cartridge through the inlet 20. The cap 14 is further provided with a gas delivery port 21 and connecting pipe 22. A flexible tube 23 shown fragmentarily is connectable with the external end of the output tube 22 and is adapted to deliver the treated gas to the patient.

Figure 3:
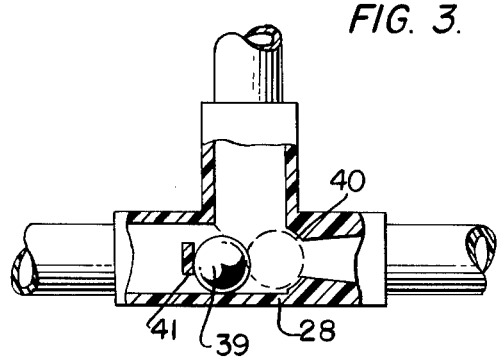
FIG. 3 is a cross sectional view of the first T structure showing the ball valve and stop elements of the structure in more detail.

A liquid or water bottle reservoir means shown in the drawings is preferably of the aforesaid sealed Concha ® unit placed in an inverted condition. The unit is a disposably sealed plastic container of aseptic water. The container comprises a principal chamber 24 when inverted, as noted in the drawings, the bottle at its lower end terminates in a neck-like outlet 25 provided with a breachable seal and adapted to be connected to the end of a flexible conduit tube 26. The essential feature of this invention resides in the method of connecting the bottle 16 with the humidifier cartridge 14 and with the elements designed to maintain the pressure in the reservoir 17 constant. The tube 26 is connected to one side 27 of first T member 28. The other side 29 of the first T member is connected through a tube 30 to the nipple 20 on the bottom of the humidifier structure. The upstanding arm 31 is connected to the line 32 which is connected to the second T member 33. One of the ends of the nipple 33 is connected to a tube 34 to the nipple 35 on the cap of the humidifier. The other conduit of the T shaped member is connected to the line 36 of the restrictor 37 and then to the nipple 38 on the reservoir 17. Details of the first T fitting are shown in FIG. 3. The inner portion of the T 28 contains a ball member 39 sufficient to close the orifice 40 as shown in FIG. 3. The ball member 39 moves between the orifice 40 and the stop 41 depending on the level of water in the bottle 17.

In operation of the system the ball valve 39 acts as a check valve in the line 26–30 to bottle 17 to the nebulizer 15. The water is transferred from the bottle 17 only when the pressure in the humidifier 14 is below that on the reservoir.

The restrictor 37 in the line 36 has a diameter of about 0.010 to 0.030 cm. and acts to maintain the pressure in the reservoir at a constant value. The maximum pressure in the reservoir is approximately 50 cm. $H_2O$ so that this reservoir no longer acts as a compliant factor in the system. The reservoir does not expand and contract in operation of the system.

While one preferred embodiment has been illustrated and described in detail it is apparent that other modifications and changes may be made by those skilled in the art without departing from the inventive spirit thereof. References should be made to the appending claims for the inventive scope covered by this invention.

What is claimed is:

1. A pediatric cartridge humidifying apparatus for humidifying and heating a breathable gas such as oxygen supplemented air to be inhaled by a pediatric patient undergoing inhalation therapy comprising:
    (a) a humidifier cartridge module means embodying a tubular cartridge main body portion with an inner peripheral wall;
    (b) said cartridge module means including an upper end portion with cap means attached to said main body;
    (c) said humidifier cartridge module means including a lower end portion terminating in a transverse wall and adapted and constructed to retain a humidifying liquid, said transverse wall having liquid inlet means adapted to be fluidly connected via conduit means with a liquid outlet means of an external liquid source;
    (d) said humidifier cartridge module means further comprising liquid absorption means including an open center generally tubular liquid-absorption column member with an inner-peripheral face constituting an evaporating surface for humidifying liquid disposed generally contiguously and coextensive with a substantial part of said cartridge main body and said lower end portion adapted and constructed to be wetted directly by the humidifying liquid when liquid is in said lower end portion, and to convey by capillary action the liquid upwardly of said absorption means and onto said evaporating surface;
    (e) said upper end portion cap means of said humidifier cartridge module means of paragraph (b) together with a portion of said main body providing an air space above the humidifying liquid level in said lower end portion of said paragraph (c) when liquid is in said lower end portion;
    (f) said cap means including a breathable gas inlet feed pipe for directing gas to be humidified into said module and terminating in said main body;
    (g) said cap means further including an outwardly projecting humidified breathable gas outlet delivery pipe in fluid communication with said air space, said delivery pipe adapted to be connected with an output delivery tube leading to a pediatric patient;
    (h) a disposable reservoir of aseptic liquid sealed therein, said disposable reservoir having a liquid outlet pipe, means for detachably mounting said reservoir externally of said module means, and liquid inlet means adapted to fluidly connect via conduit means with said liquid outlet means of said external reservoir of aseptic liquid with said module means wherein said conduit means comprises a first tubular T shaped member having a check valve positioned therein, one of the two horizontal ends of said first tubular T shaped member connecting to the inlet of said module, the other horizontal end of said first T shaped member connecting to the liquid outlet of said reservoir, the vertical end of said first tubular T shaped member connecting to a second tubular T shaped member contiguous to the top portion of said module, one of the two other ends of said second tubular T shaped member connecting to said upper-end-portion cap means, the other of said two other ends of said second tubular T shaped member connecting through a restrictor to said reservoir of aseptic liquid.

2. The apparatus according to claim 1 wherein the check valve in said first T shaped conduit member is a ball valve.

3. The apparatus according to claim 2 wherein said ball is of a size sufficient to close the liquid outlet from said reservoir.

4. The apparatus according to claim 2 wherein said first T shaped conduit contains a stop means to limit the movement of the ball of said ball valve.

5. The apparatus according to claim 1 wherein the restrictor in said second T shaped member has a diameter of 0.010 to 0.030 centimeters.

* * * * *